United States Patent
Pignato et al.

(10) Patent No.: US 10,632,303 B2
(45) Date of Patent: Apr. 28, 2020

(54) ADAPTER FOR CONNECTION TO PULSE GENERATOR

(71) Applicant: CVRx, Inc., Minneapolis, MN (US)

(72) Inventors: Paul Pignato, Stacy, MN (US); Vance Kesler, Roseville, MN (US); Adam Cates, Delano, MN (US); Bart Carey, Maplewood, MN (US); Greg Sundberg, Stillwater, MN (US); Joe DuPay, Andover, MN (US); Luis Miguel Rodriguez, Shoreview, MN (US)

(73) Assignee: CVRx, Inc., Minneapolis, MN (US)

( * ) Notice: Subject to any disclaimer, the term of this patent is extended or adjusted under 35 U.S.C. 154(b) by 327 days.

(21) Appl. No.: 15/136,361

(22) Filed: Apr. 22, 2016

(65) Prior Publication Data

US 2016/0235968 A1    Aug. 18, 2016

Related U.S. Application Data

(62) Division of application No. 13/959,336, filed on Aug. 5, 2013, now Pat. No. 9,345,877.

(51) Int. Cl.
  *A61N 1/05* (2006.01)
  *A61N 1/375* (2006.01)
  *A61N 1/36* (2006.01)

(52) U.S. Cl.
  CPC ........ *A61N 1/0551* (2013.01); *A61N 1/36117* (2013.01); *A61N 1/3752* (2013.01)

(58) Field of Classification Search
  CPC ...... A61N 1/0553; A61N 1/0558; A61N 1/08; A61N 1/3752; A61N 1/3754; A61N 1/0563; A61N 1/0592; A61N 1/0595; A61N 2001/058; A61N 1/3756; A61N 1/3758; A61N 1/05; A61N 1/36185; A61N 1/36128; A61N 1/36135; A61N 1/36139
  USPC .......................................................... 607/44
  See application file for complete search history.

(56) References Cited

U.S. PATENT DOCUMENTS

| | | |
|---|---|---|
| 4,699,147 A | 10/1987 | Chilson et al. |
| 5,411,539 A | 5/1995 | Neisz |
| 5,557,210 A * | 9/1996 | Cappa ..................... A61N 1/05 324/538 |
| 5,772,690 A | 1/1998 | Kroll |
| 5,964,793 A | 10/1999 | Rutten et al. |

(Continued)

OTHER PUBLICATIONS

Application and File History for U.S. Appl. No. 13/959,336, filed Aug. 5, 2013, inventors Pignato et al.

*Primary Examiner* — Darwin P Erezo
*Assistant Examiner* — Katherine H Schwiker
(74) *Attorney, Agent, or Firm* — Patterson Thuente Pedersen, P.A.

(57) ABSTRACT

Embodiments of the present invention generally pertain to devices and methods for use in conjunction with implanting a baroreflex therapy system which includes an implantable pulse generator and associated circuitry contained within a hermetically sealed housing, an elongate flexible electrical lead connectable to the housing, and a monopolar electrode structure coupled with the electrical lead. More specifically, the devices and methods of the present invention allow for a mapping procedure to be conducted as part of the implant procedure prior to fully implanting the baroreflex therapy system.

12 Claims, 11 Drawing Sheets

(56) References Cited

U.S. PATENT DOCUMENTS

| | | | |
|---|---|---|---|
| 6,522,926 | B1 | 2/2003 | Kieval et al. |
| 6,725,096 | B2 | 4/2004 | Chinn et al. |
| 6,850,801 | B2 | 2/2005 | Kieval et al. |
| 6,985,774 | B2 | 1/2006 | Kieval et al. |
| 7,480,532 | B2 | 1/2009 | Kieval et al. |
| 7,499,747 | B2 | 3/2009 | Kieval et al. |
| 7,835,797 | B2 | 11/2010 | Rossing et al. |
| 7,840,271 | B2 | 11/2010 | Kieval et al. |
| 8,086,314 | B1 | 12/2011 | Kieval et al. |
| 8,326,430 | B2 | 12/2012 | Georgakopoulos et al. |
| 8,437,867 | B2 | 5/2013 | Murney et al. |
| 8,620,422 | B2 | 12/2013 | Kieval et al. |
| 9,345,877 | B2 | 5/2016 | Pignato et al. |
| 2006/0004417 | A1 | 1/2006 | Rossing et al. |
| 2006/0074453 | A1 | 4/2006 | Kieval et al. |
| 2006/0253181 | A1 | 11/2006 | Schulman et al. |
| 2008/0082137 | A1 | 4/2008 | Kieval et al. |
| 2010/0137934 | A1* | 6/2010 | Doerr .................. A61N 1/3752 607/28 |
| 2012/0109250 | A1 | 5/2012 | Cates et al. |
| 2013/0018444 | A1* | 1/2013 | Glenn ..................... A61N 1/05 607/116 |
| 2015/0038978 | A1 | 2/2015 | Pignato et al. |

\* cited by examiner

US 10,632,303 B2

ADAPTER FOR CONNECTION TO PULSE GENERATOR

CROSS-REFERENCE TO RELATED APPLICATIONS

This application is a Divisional of U.S. application Ser. No. 13/959,336, filed Aug. 5, 2013, now U.S. Pat. No. 9,345,877, titled "ADAPTER FOR CONNECTION TO PULSE GENERATOR," the disclosure of which is hereby incorporated by reference in its entirety.

FIELD OF THE INVENTION

The present invention relates generally to implantable medical devices and associated methods for implanting such devices, and more particularly the present invention relates to an adapter for use during an implant procedure of such devices.

BACKGROUND OF THE INVENTION

Cardiovascular disease is a major contributor to patient illness and mortality. It also is a primary driver of health care expenditure, costing billions of dollars each year in the United States. Heart failure is the final common expression of a variety of cardiovascular disorders, including ischemic heart disease. It is characterized by an inability of the heart to pump enough blood to meet the body's needs and results in fatigue, reduced exercise capacity and poor survival. Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

Hypertension, or high blood pressure, is a major cardiovascular disorder that is estimated to affect 65 million people in the United States alone. Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Hypertension is a leading cause of heart failure and stroke, is the primary cause of death for tens of thousands of patients per year, and is listed as a primary or contributing cause of death for hundreds of thousands of patients per year in the U.S. Accordingly, hypertension is a serious health problem demanding significant research and development for the treatment thereof. Hypertension remains a significant risk for patients and challenge for health care providers around the world despite improvements in awareness, prevention, treatment and control over the last 30 years. Patients with hypertension are encouraged to implement lifestyle modifications including weight reduction, adopting the DASH eating plan, reducing dietary sodium, increasing physical activity, and limiting alcohol consumption and smoking. A large number of pharmacologic treatments are also currently available to treat hypertension.

An improved approach for treating hypertension, heart failure and/or other cardiovascular disorders has been developed. Baroreflex Activation Therapy ("BAT") utilizes electrical, mechanical, chemical, and/or other means of stimulation to activate one or more components of a patient's baroreflex system, such as baroreceptors. Baroreceptors are sensory nerve ends that are profusely distributed within the arterial walls of the major arteries, as well in the heart, aortic arch, carotid sinus or arteries, and in the low-pressure side of the vasculature such as the pulmonary artery and vena cava. Baroreceptor signals are used to activate a number of body systems which collectively may be referred to as the baroreflex system. Baroreceptors are connected to the brain via the nervous system, allowing the brain to detect changes in blood pressure, which is indicative of cardiac output. If cardiac output is insufficient to meet demand (i.e., the heart is unable to pump sufficient blood), the baroreflex system activates a number of body systems, including the heart, kidneys, vessels, and other organs/tissues. Such natural activation of the baroreflex system generally corresponds to an increase in neurohormonal activity. Specifically, the baroreflex system initiates a neurohormonal sequence that signals the heart to increase heart rate and increase contraction force in order to increase cardiac output, signals the kidneys to increase blood volume by retaining sodium and water, and signals the vessels to constrict to elevate blood pressure. The cardiac, renal and vascular responses increase blood pressure and cardiac output, and thus increase the workload of the heart. In a patient suffering from heart failure, this further accelerates myocardial damage and exacerbates the heart failure state.

One of the first descriptions of treating hypertension through baroreceptor stimulation appears in U.S. Pat. No. 6,522,926 to Kieval et al., which discloses devices and methods for stimulating or activating baroreceptors or the baroreflex system to regulate blood pressure and/or treat other cardiovascular disorders. Generally speaking, a baroreceptor activation device may be activated, deactivated or otherwise modulated to activate one or more baroreceptors and induce a baroreceptor signal or a change in the baroreceptor signal to thereby affect a change in the baroreflex system. The baroreceptor activation device may be activated, deactivated, or otherwise modulated continuously, periodically, or episodically. The baroreceptor activation device may utilize electrical as well as mechanical, thermal, chemical, biological, or a combination thereof to activate the baroreceptor. The baroreceptor may be activated directly, or activated indirectly via the adjacent vascular tissue. Activation of this reflex increases afferent electrical signals through the carotid sinus nerve (Hering's nerve, a branch of the glossopharyngeal nerve, cranial nerve IX) to the medullary brain centers that regulate autonomic tone. Increased afferent signals to these medullary centers cause a reduction in sympathetic tone and an increase in parasympathetic tone. This results in lower heart rate, reduced sodium and water reabsorption by the kidney resulting in a diuresis, relaxation of the smooth muscle in the blood vessels which results in vasodilatation and a reduction in blood pressure. Thus, peripheral activation of the baroreflex results in a physiologic response whereby blood pressure is controlled by mechanisms determined by the integrative action of the central nervous system action on all peripheral organs and blood vessels.

The process of implanting a baroreflex activation device, such as an electrode assembly, for delivering baroreflex therapy is known as mapping—positioning the assembly such that the electrodes are properly situated against the wall of a vessel containing baroreceptors, and securing the electrode assembly to the artery so that the positioning is maintained.

Mapping adds to the overall procedure time due to adjusting and re-adjusting the position of the electrode assembly during implantation. Present-day procedures involve positioning and holding the electrode assembly in place with forceps, hemostat or similar tool while applying the stimulus and observing the response in the patient. Movement by as little as 1 mm can make a medically relevant difference in the effectiveness of the baroreceptor activation.

The positioning is a critical step, as the electrodes must direct as much energy as possible toward the baroreceptors for maximum effectiveness and efficiency. The energy source for the implanted baroreflex stimulation device is typically an on-board battery with finite capacity, and it is desirable to provide a lower energy source to ensure patient safety. A high-efficiency implantation will provide a longer battery life and correspondingly longer effective service life between surgeries because less energy will be required to achieve the needed degree of therapy. As such, during implantation of the electrode assembly, the position of the assembly is typically adjusted several times during the implantation procedure in order to optimize the baroreflex response. One example of mapping methods and techniques for implanting electrodes is disclosed in U.S. Pat. No. 6,850,801 to Kieval et al.

Current generation implantable baroreflex therapy systems, such as described in U.S. Pat. No. 8,437,867 to Murney et al., include an implantable pulse generator and associated circuitry contained within a hermetically sealed housing, an elongate flexible electrical lead connectable to the housing, and a monopolar electrode structure coupled with the electrical lead. As used herein, the words "housing," "enclosure," "case" and "can" are synonymous when used to refer to the housing of the implantable pulse generator. At least a portion of the housing is conductive for use as an electrode in conjunction with the monopolar electrode structure on the lead. Such a housing may be referred to as an active can.

The mapping procedure may be performed with some or all components of the implantable baroreflex therapy system. While it would be possible to conduct the mapping procedure utilizing specialized equipment retained by the hospital or clinic, such as one or more temporary and/or reusable leads which are connectable to an external pulse generator, this equipment increases the overall cost, complexity and time of the mapping procedure. Thus, it is desirable to utilize as many of the implantable system components as possible for the mapping procedure.

Further, it is desirable to perform the mapping procedure prior to fully implanting the therapy system. Creating a pocket in the chest of the patient placement of the implantable pulse generator may require use of anesthetics which can impact the mapping procedure by altering the patient's response, and leaving such a pocket open during the mapping procedure increases the risk of infection. Thus it is desirable to refrain from creating a pocket in the chest of the patient for placement of the implantable pulse generator, and/or refrain from tunneling a path for the lead from the pocket to the electrode implant site, until it has been confirmed through the mapping procedure that a suitable patient response has been obtained. In the event a suitable response from the patient cannot be obtained during the mapping procedure, the implant procedure may be postponed or terminated.

However, because current generation implantable baroreflex therapy systems utilize a monopolar electrode structure in combination with an active can (the housing of the implantable pulse generator is electrically conductive to create a return path from the electrode structure), a problem exists for performing the mapping procedure without creating a pocket in the chest of the patient for the implantable pulse generator.

A need therefore exists for more cost- and time-effective devices and methods for performing a mapping procedure as part of implanting a baroreflex therapy system.

SUMMARY OF THE INVENTION

In one embodiment, the present invention comprises a system including a control system contained within an implantable housing, an electrical lead, coupleable to the control system, a monopolar electrode coupled to the electrical lead, the electrode being configured for implantation in contact with at least a portion of a blood vessel, a reference element, configured to be temporarily inserted subcutaneously in a patient, and an implant adapter, including a first end configured to couple with the housing and a second end configured to couple with the reference element, wherein the first end and second end are conductively coupled.

In another embodiment, the present invention comprises a method of implanting a baroreflex activation system within a patient, the system including a control system contained within an implantable housing, an electrical lead, and a monopolar electrode coupled to the electrical lead. The method comprises creating an incision in a patient, coupling the electrical lead to a header of the housing, inserting a temporary reference element subcutaneously into the patient, coupling an adapter between the temporary reference element and the housing, conducting a mapping procedure to determine a suitable implant location for the electrode proximate a blood vessel, the mapping procedure using the monopolar electrode and the reference element, the mapping procedure being conducted while the housing is not implanted in or in contact with the patient, securing the electrode at the suitable implant location, removing the adapter, and implanting the electrical lead and the housing into the patient.

In another embodiment, the present invention comprises a method, comprising providing a baroreflex activation system, the system including a control system contained within an implantable housing, an electrical lead, and a monopolar electrode coupled to the electrical lead. The method further comprises providing an implant kit, the kit including a reference element, configured to be inserted subcutaneously in a patient, and an implant adapter, including a first end configured to couple with the housing and a second end configured to couple with the reference element, wherein the first end and second end are conductively coupled. The method further comprises providing instructions to the user, comprising creating an incision in a patient, coupling the electrical lead to a header of the housing, inserting a temporary reference element subcutaneously into the patient, coupling an adapter between the temporary reference element and the housing, conducting a mapping procedure to determine a suitable implant location for the electrode proximate a blood vessel, the mapping procedure using the monopolar electrode and the reference element, the mapping procedure being conducted while the housing is not implanted in or in contact with the patient, securing the electrode at a selected implant location, removing the adapter, and implanting the electrical lead and the housing into the patient.

As used herein, providing a system or device may comprise manufacturing and distributing the system or device to a user, or may comprise causing the system or device to be manufactured and made available to a user. Typical users may include hospitals, clinics, surgeons or medical device distributors.

BRIEF DESCRIPTION OF THE DRAWINGS

The invention may be more completely understood in consideration of the following detailed description of various embodiments of the invention in connection with the accompanying drawings, in which.

Figure 1:
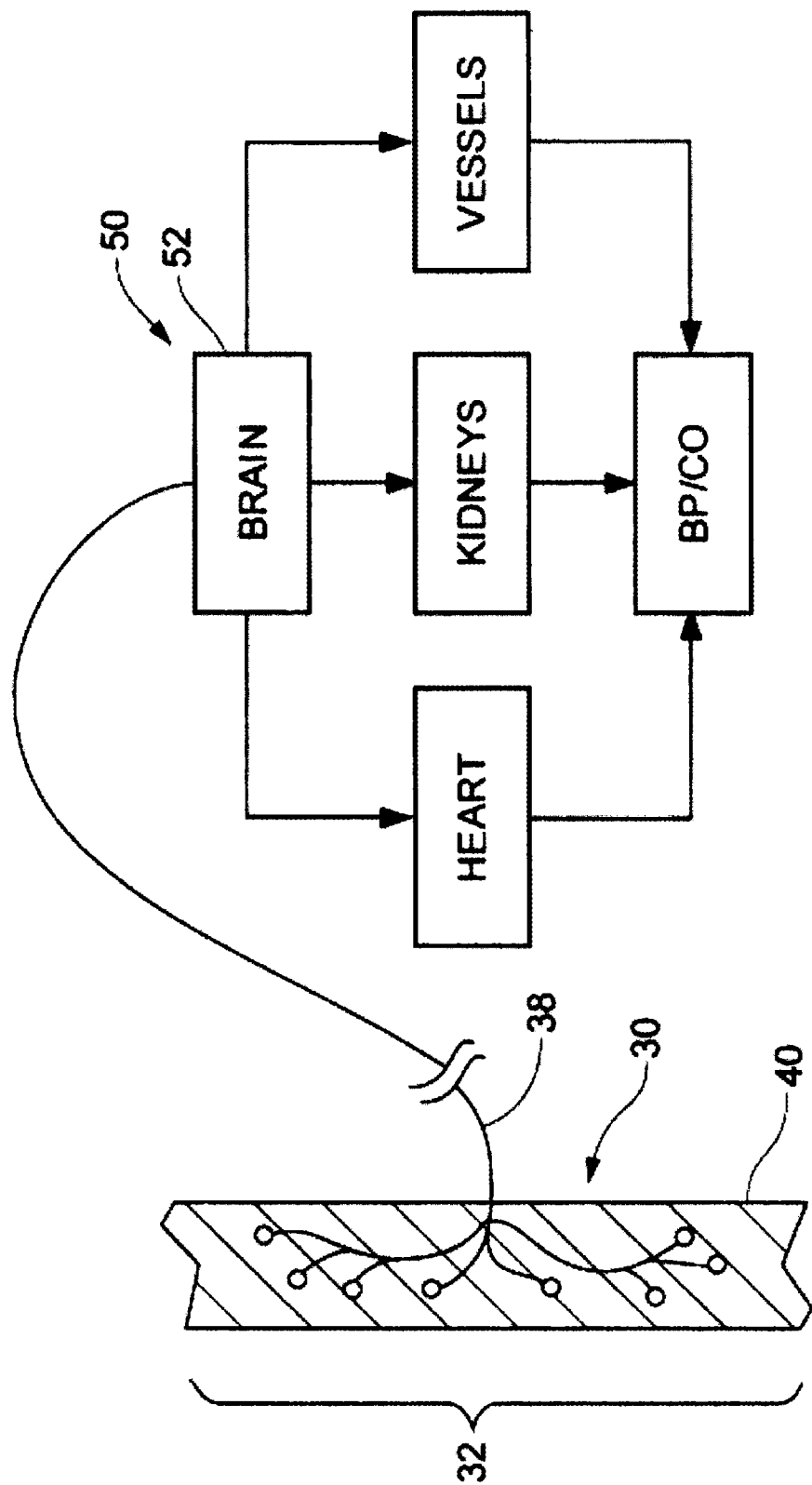
FIG. 1 is a cross-sectional schematic illustration of baroreceptors within the vascular wall and the baroreflex system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Embodiments of the present invention generally pertain to devices and methods for use in conjunction with implanting a baroreflex therapy system. More specifically, such devices and methods allow for a mapping procedure to be conducted as part of the implant procedure, prior to fully implanting the baroreflex therapy system.

Refer now to FIG. 1, which depicts a schematic illustration of baroreceptors 30 disposed in a generic vascular wall 40 and a schematic flow chart of the baroreflex system 50. Baroreceptors 30 are profusely distributed within the vascular walls discussed previously, and generally form an arbor 32. The baroreceptor arbor 32 comprises a plurality of baroreceptors 30, each of which transmits baroreceptor signals to the brain 52 via nerve 38. In some locations, the baroreceptors 30 are profusely distributed and arborized within the vascular wall 40 such that discrete baroreceptor arbors 32 are not readily discernable. To this end, those skilled in the art will appreciate that the baroreceptors 30 depicted in FIG. 1 are primarily schematic for purposes of illustration and discussion. In other regions, the baroreceptors may be so sparsely distributed that activation over a relatively greater length of the vein would be required than would be with an artery where the receptors might be more concentrated.

Baroreceptor signals in the arterial vasculature are used to activate a number of body systems which collectively may be referred to as the baroreflex system. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, various embodiments of the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of some embodiments of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Stimulation of the baroreflex system may be accomplished by stimulating such receptors, nerves, nerve fibers, or nerve endings, or any combination thereof.

For additional information pertaining to the cardiovascular, circulatory and nervous systems, as well as baroreceptor and baroreflex therapy systems that may be used in whole or in part with embodiments of the present invention, reference is made to the following commonly assigned published applications and patents: U.S. Published Patent Application Nos. 2006/0004417 to Rossing et al., 2006/0074453 to Kieval et al., 2008/0082137 to Kieval et al., and U.S. Pat. No. 6,522,926 to Kieval et al., U.S. Pat. No. 6,850,801 to Kieval et al., U.S. Pat. No. 6,985,774 to Kieval et al., U.S. Pat. No. 7,480,532 to Kieval et al., U.S. Pat. No. 7,499,747 to Kieval et al., U.S. Pat. No. 7,835,797 to Rossing et al., U.S. Pat. No. 7,840,271 to Kieval et al., U.S. Pat. No. 8,086,314 to Kieval, U.S. Pat. No. 8,326,430 to Georgakopoulos et al., and U.S. Pat. No. 8,437,867 to Murney et al., the disclosures of which are hereby incorporated by reference in their entireties except for the claims and any expressly contradictory definitions.

Generally, implantable baroreflex activation systems include a control system, a baroreceptor activation device, one or more optional sensors, and an optional programming device. The baroreceptor activation device may comprise a wide variety of devices which utilize mechanical, electrical, thermal, chemical, biological, or other means to activate one or more baroreceptors. The baroreceptor may be activated directly, or activated indirectly via the adjacent vascular tissue. According to various embodiments, the baroreceptor activation device may be positioned intravascularly (e.g., inside the vascular lumen); extravascularly (outside of the vessel, e.g., disposed on the outer surface of the vessel, or in contact with at least a portion of the vessel, or proximate the vessel); transvascularly (e.g., at least a portion of the device being intravascular and at least a portion of the device being extravascular, or at least a portion of the device being in a first vessel and at least a portion of the device being in a second, neighboring vessel); intramurally (e.g., within the vascular wall); around all or a portion of a vascular sheath structure surrounding at least one vein and one artery as well as associated nerve structures; or on, about or otherwise in contact with associated tissues in the extravascular space proximate a blood vessel; or otherwise positioned proximate tissue in which baroreceptors reside.

Figure 2:
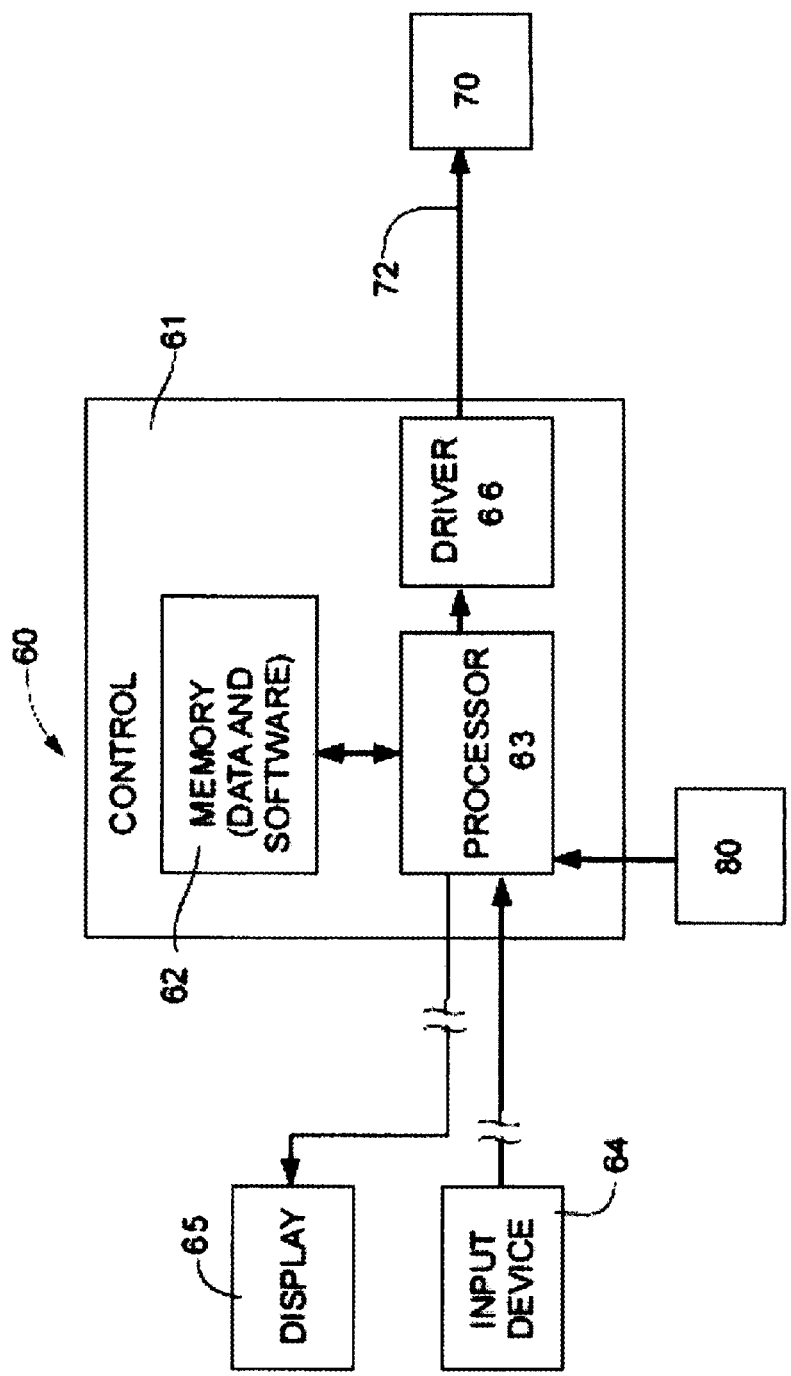
FIG. 2 is a schematic illustration of a baroreceptor activation system in accordance with the present invention.

A baroreflex activation therapy system according to embodiments of the present invention generally include a control system, a baroreceptor activation device, and a lead. Referring now to FIG. 2, one embodiment of an implantable baroreflex therapy system 90 is depicted, which includes a control system 60, a baroreflex activation device 70, a lead 72, one or more optional sensor(s) 80, and an input device (programmer) 64 configured to communicate with control system 60. The control system 60 includes a therapy block 61 comprising one or more associated processors 63, and a memory 62 adapted to store one or more algorithms which define a stimulus (or therapy) regimen which dictates the characteristics of the control signal as a function of time, and thus dictates the stimulation of baroreceptors as a function of time. An example of an implantable therapy system 90 suitable for use with embodiments of the present invention is the CVRx Barostim NEO System, CE marked and approved for sale in Europe and available for investigational use in the United States.

Control system 60 includes a driver 66 to provide the desired power mode for the baroreflex activation device 70. For example, if baroreflex activation device 70 utilizes electrical actuation, the driver 66 may comprise a power amplifier, a pulse generator or the like to selectively deliver electrical control signals, and the cable 72 may comprise electrical lead(s). Control system 60 is enclosed within a housing (or can) 68, and is communicably coupled to baroreflex activation device 70 such as by way of electric control cable 72 (e.g., electric lead), or by wireless means such as radiofrequency or other forms of wireless communication. Lead 72 may include an optional attachment tab 73, which may be used to suture or otherwise attach lead 72 to a patient in order to provide strain relief to the electrode-tissue interface.

As depicted in FIG. 2, control system 60, activation device 70, lead 72 and optional sensor 80 are configured to be implanted within the patient, while programmer device 64 and display 65 are configured to be external to the patient and operably communicate with control system 60 through wireless or wired connections. In another embodiment, programmer device 64 includes a display 65.

In one embodiment in which driver 66 comprises a pulse generator, control system 60 may simply be referred to as the pulse generator, which is understood to encompass not only driver 66 but also the necessary circuitry and components for generating and delivering control signals to baroreflex activation device 70, as well as housing 68. The control signal may alternately be referred to as an output signal, a therapy signal, a therapy output signal, or simply a pulse. Such a pulse generator and associated circuitry may be enclosed within hermetically sealed housing 68 configured for implantation into the patient. The pulse generator housing 68 may include a header 69 adapted to facilitate connection of one or more leads 72, as well as a case electrode 67 on at least a portion of the outer surface of housing 68. Electrode 67 may also be referred to as an indifferent electrode, common electrode, or reference electrode.

Alternately, the entire surface of housing 68 may be conductive so as to comprise electrode 67. Lead 72 generally includes a proximal end having a connector for coupling to header 69 of pulse generator housing 68, a body portion, and a distal end. In one embodiment, baroreceptor activation device 70 is disposed on the distal end of lead 72, although it will be understood that other arrangements of baroreceptor activation device 70 and lead 72 are within the spirit and scope of the present invention.

Generally, a baroreflex activation therapy system 90 according to embodiments of the present application is configured to provide a therapy signal having a voltage of between about 1-15 V, at a frequency of between about 5-200 Hz, an amplitude of between about 0.5-25 milliamps, and a pulse width of between about 10-1200 microseconds. More particularly, the therapy signal has a voltage of between about 2-10 V, at a frequency of between about 10-100 Hz, an amplitude of between about 1-20 milliamps, and a pulse width of between about 15-500 microseconds.

Figure 3A:
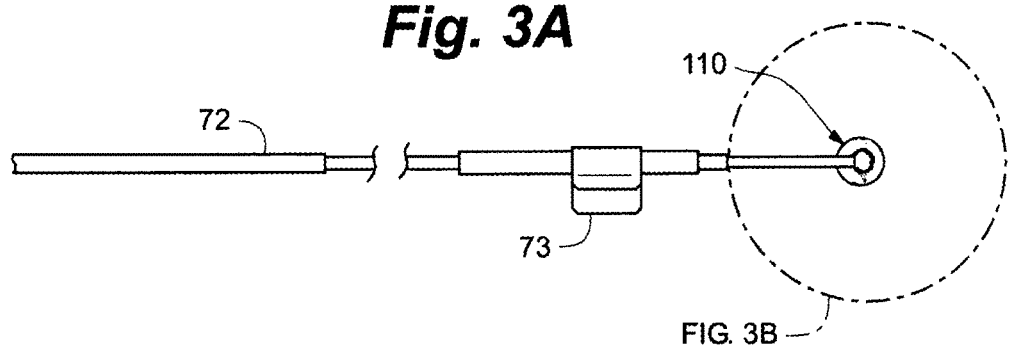
FIG. 3A is a plan view of an electrode coupled with a lead according to an embodiment of the present invention.
Figure 3B:
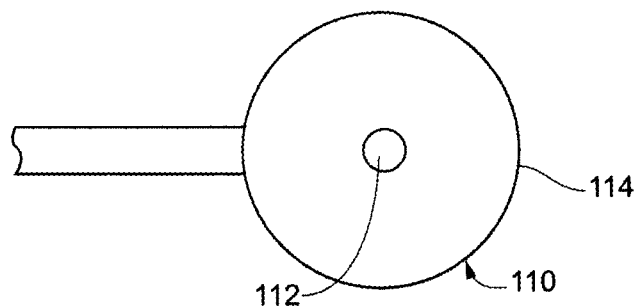
FIG. 3B is a close-up inverted view of a portion of FIG. 3A.

In one embodiment, baroreceptor activation device 70 comprises an electrode structure 110. Referring to FIGS. 3A-3B, electrode structure 110 generally includes an electrode 112 mounted on, integrated with, or otherwise coupled to a backer 114. Electrode 112 may comprise platinum iridium, and may include a surface treatment, such as iridium oxide or titanium nitride and/or can include steroid, anti-inflammatory, antibiotic and/or analgesic compounds, for example. Backer 114 may be constructed of Dacron-reinforced insulated silicone, or other suitable materials that are flexible, sturdy, electrically insulative and/or suitable for implantation in a body. Backer 114 and/or electrode 112 may comprise circular structures, or other suitable arrangements without departing from the spirit of the invention. For example, backer 114 may include one or more tabs or features configured for facilitating fixation to tissue. In one embodiment, electrode 112 may have a diameter of about 1 mm, and backer 114 may have a diameter of about 6 mm. However, it is contemplated that electrode 112 may have a diameter within a range of about 0.25 mm-3 mm, while backer 114 may have a diameter within a range of about 1 mm-10 mm. In one embodiment, the diameter of backer 114 is at least twice the diameter of electrode 112.

In one embodiment of implantable system 90, electrode 112 comprises a cathode while case electrode 67 on housing 68 of control system 60 comprises an anode. In another embodiment, an anode may be provided as part of lead 72, for example being situated along the body of lead 72. In another embodiment, an anode is provided on a second lead which is also coupled to control system 60. In all embodiments, the surface area of the anode is preferably sufficiently larger than the surface area of the cathode, for example about ten times larger. In other embodiments, the surface area of the anode may be about twenty times larger than the surface area of the cathode, up to about fifty times larger than the surface area of the cathode. Further, the anode and cathode are preferably positioned at a minimum distance away from one another, for example, the distance may be about twenty times the diameter of the cathode. In another embodiment, the distance between the anode and the cathode is at least fifty times the diameter of the cathode.

Although the remainder of the disclosure describes embodiments wherein electrode 112 comprises a cathode, it should be understood that in an alternate embodiment, electrode 112 may comprise an anode while one of case electrode 67 or an additional electrode on lead 72 comprises a cathode. Cathodic stimulation depolarizes cell membranes near the electrode, whereas anodic stimulation hyperpolarizes such membranes. The depolarization associated with cathodic stimulation tends to reduce the amount of current required from implantable control system 60 to generate action potentials within the cells and thereby stimulate baroreceptors. Thus, it will be understood that while anodic stimulation is within the scope of the present invention, cathodic stimulation is preferred.

In one embodiment, multiple electrode structures may be provided as part of a baroreflex activation therapy system 90 according to the present invention. For example, a first electrode structure 110 may be positioned at a first anatomical location such as a left carotid sinus, while a second electrode structure 110 is positioned at a second anatomical location such as a right carotid sinus. Or a first electrode structure 110 may be positioned at a first anatomical location while a second electrode structure is positioned at a second anatomical location proximate the first anatomical location, such as for example positioning first and second electrode structures proximate one another on the left carotid sinus and/or carotid arteries.

Figure 4:
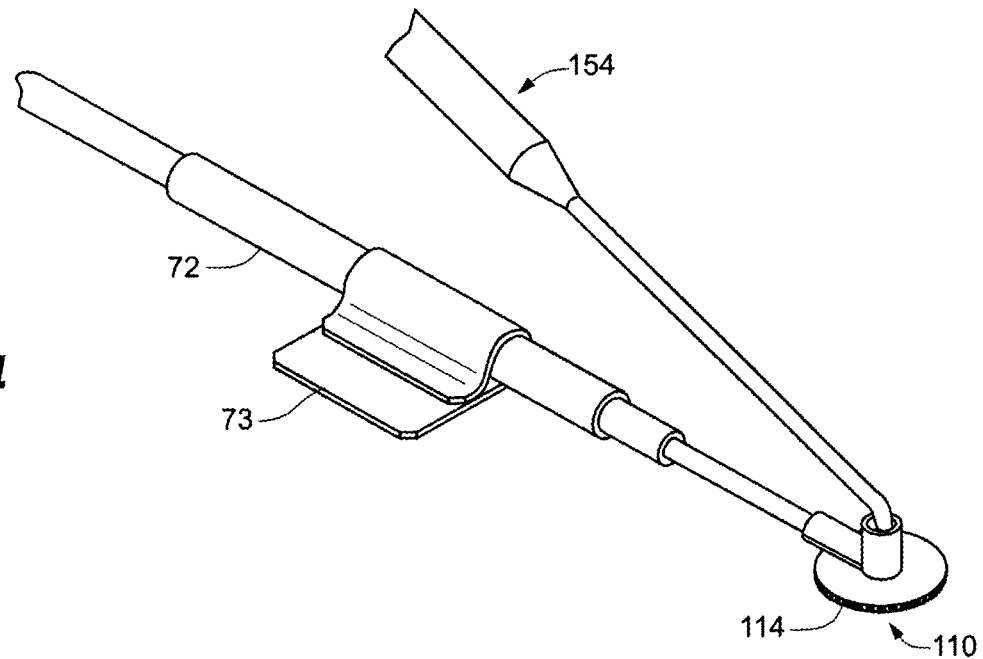
FIG. 4 is an isometric view of an implant tool engaged with an electrode structure according to an embodiment of the present invention.

Electrode structure 110 also includes an interface means configured for coupling with an implant tool 154, as depicted in FIG. 4 and as described in further detail in U.S. Pat. No. 8,437,867 to Murney et al., incorporated by reference above. Such an implant tool may be utilized to manipulate electrode structure 110 during a mapping procedure.

Figure 5A:
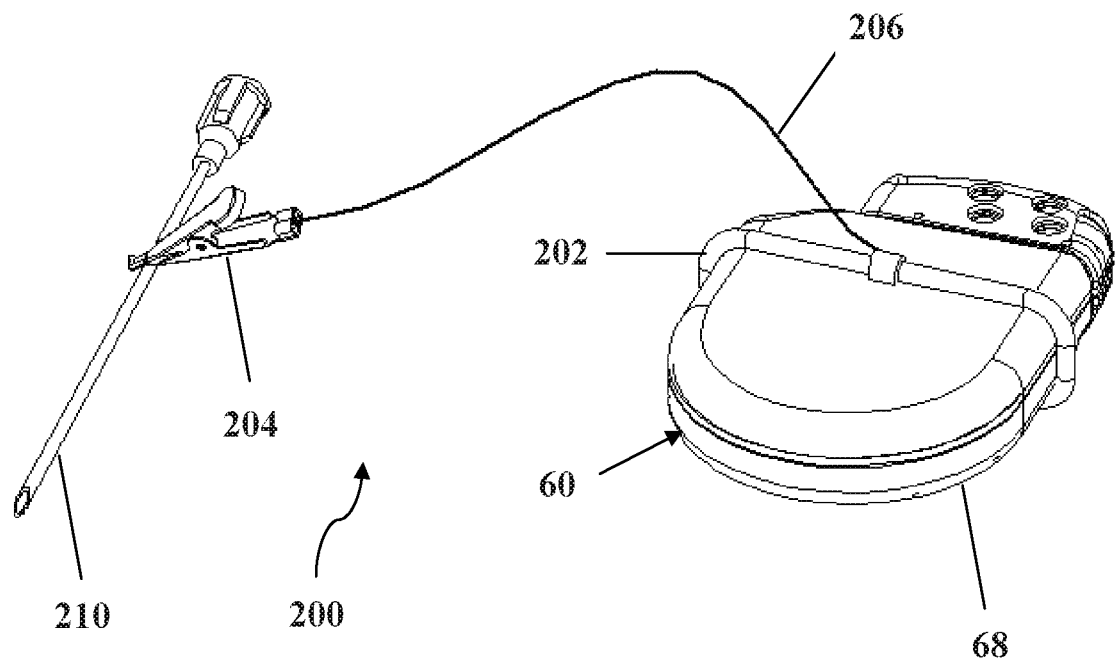
FIGS. 5A-5H are isometric views of an implant adapter engaged with a pulse generator housing according to embodiments of the present invention.
Figure 5B:
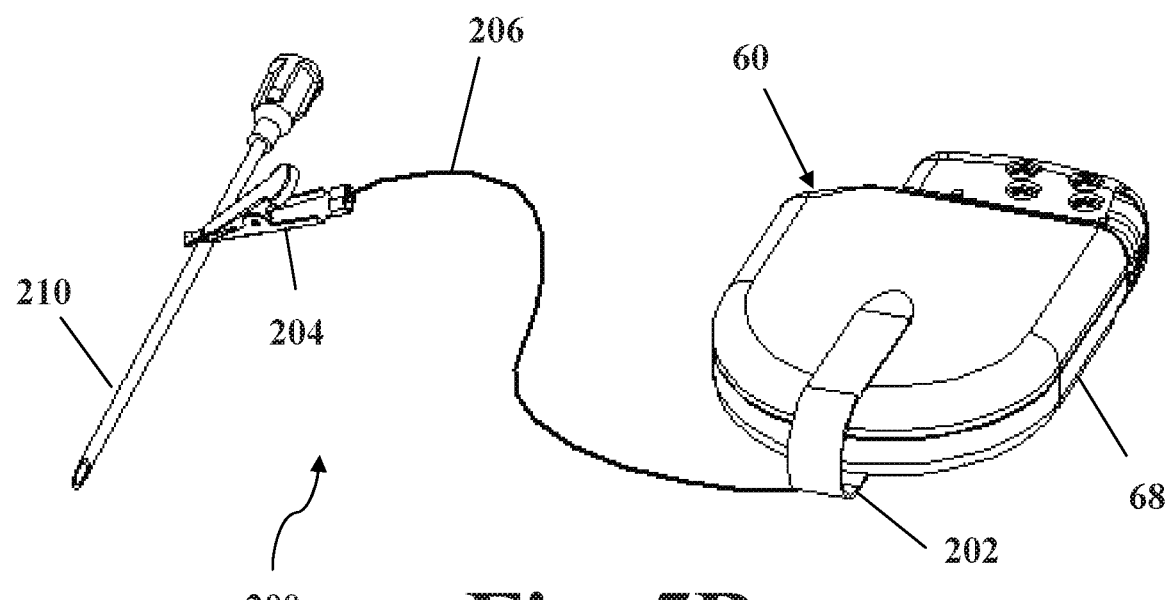
Figure 5C:
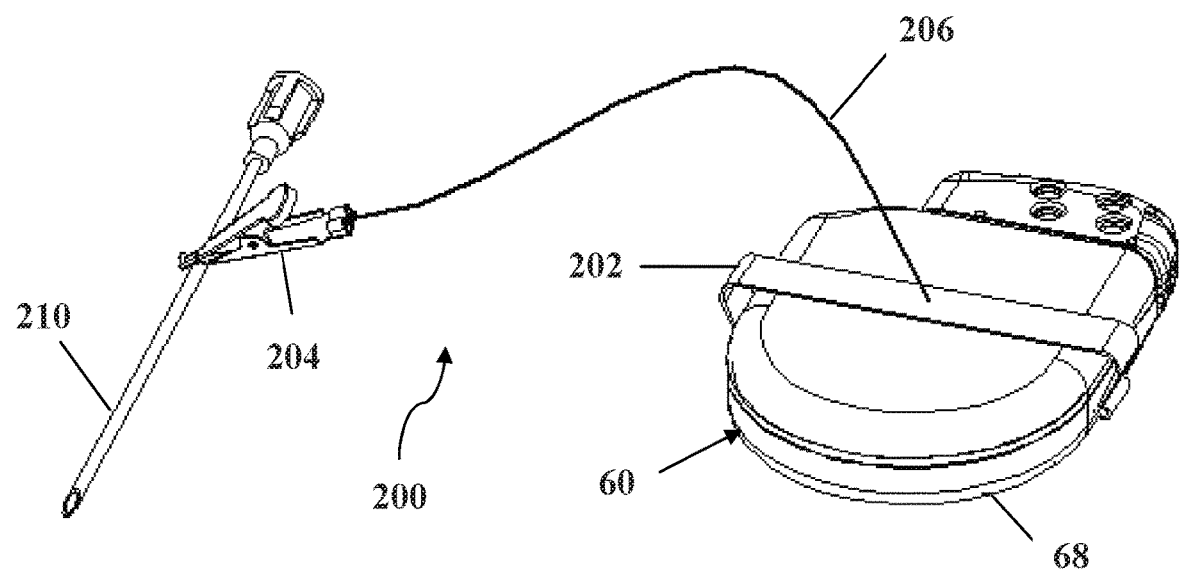
Figure 5D:
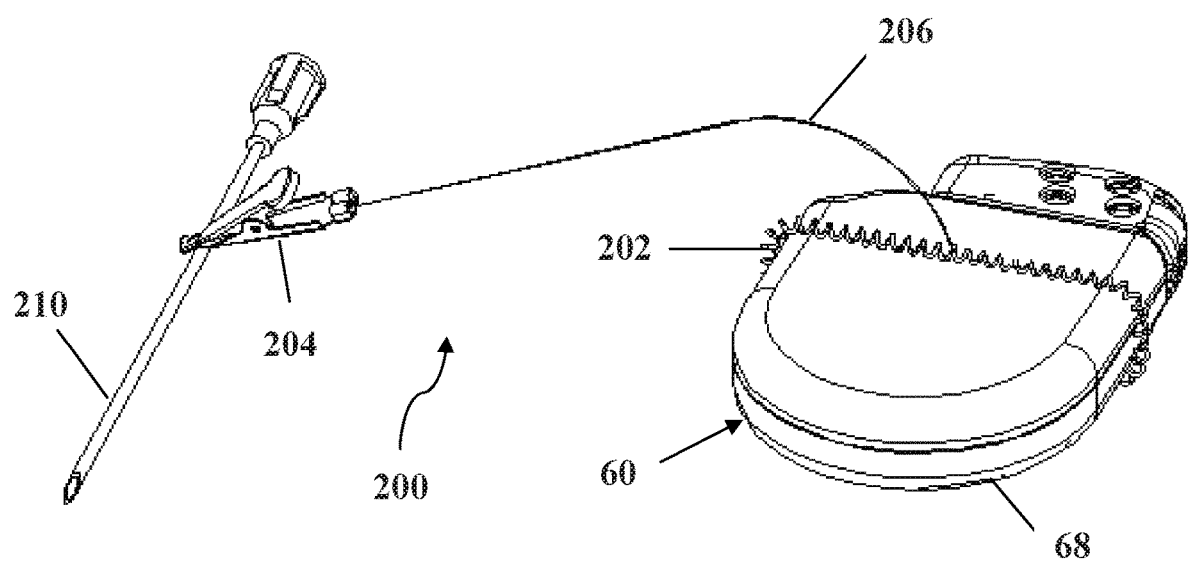
Figure 5E:
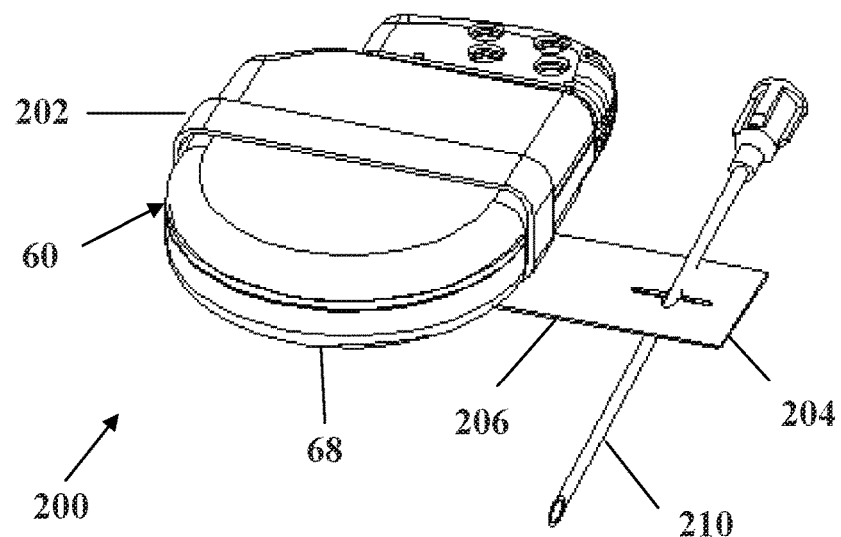
Figure 5F:
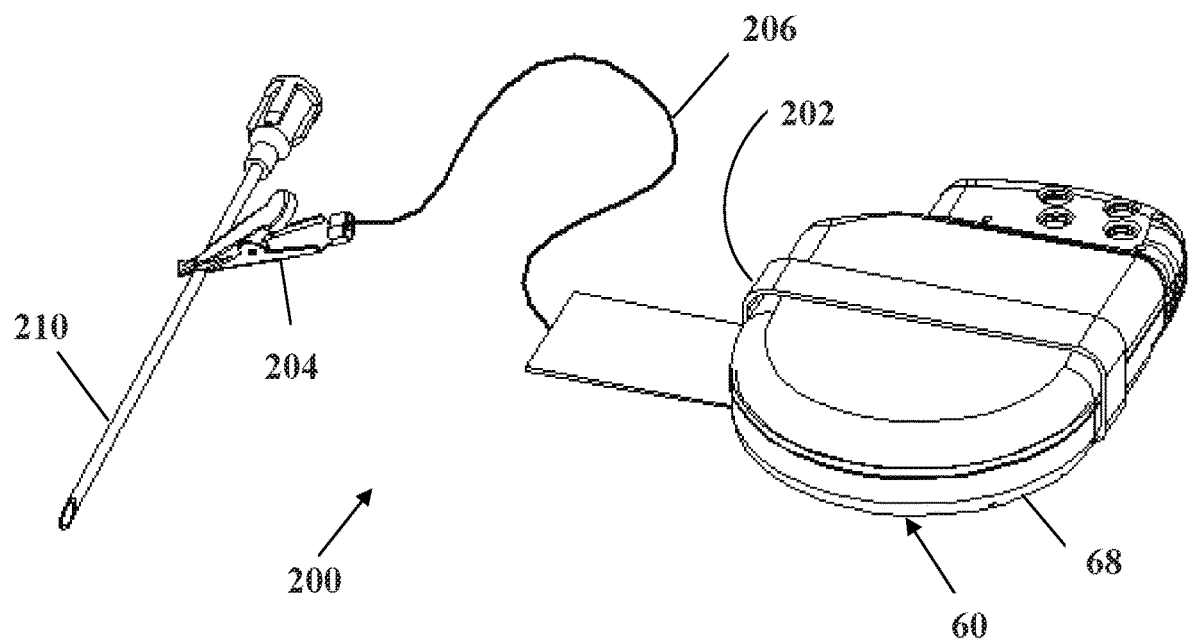
Figure 5G:
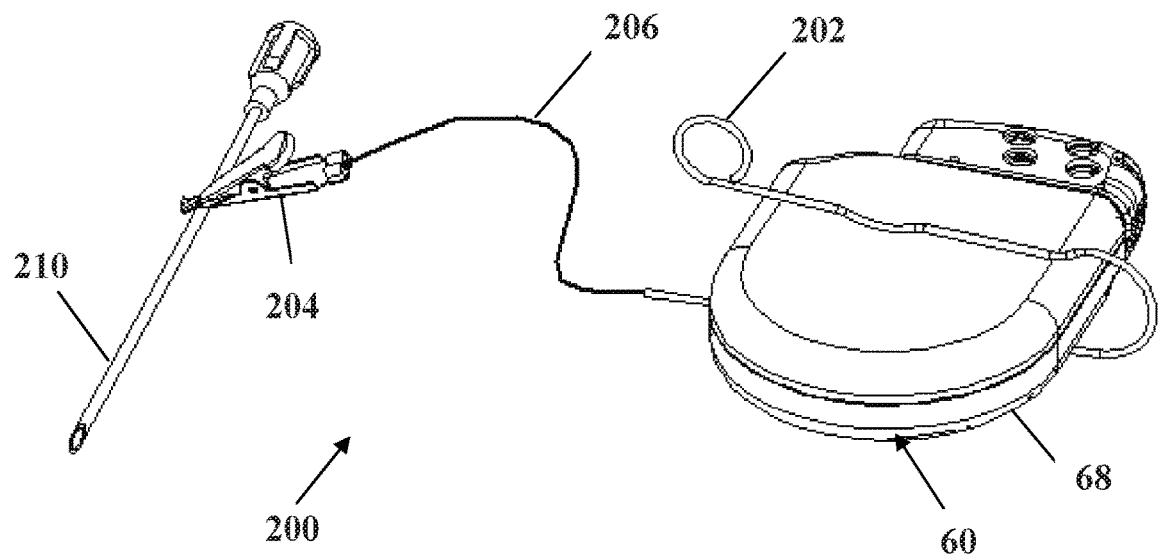
Figure 5H:
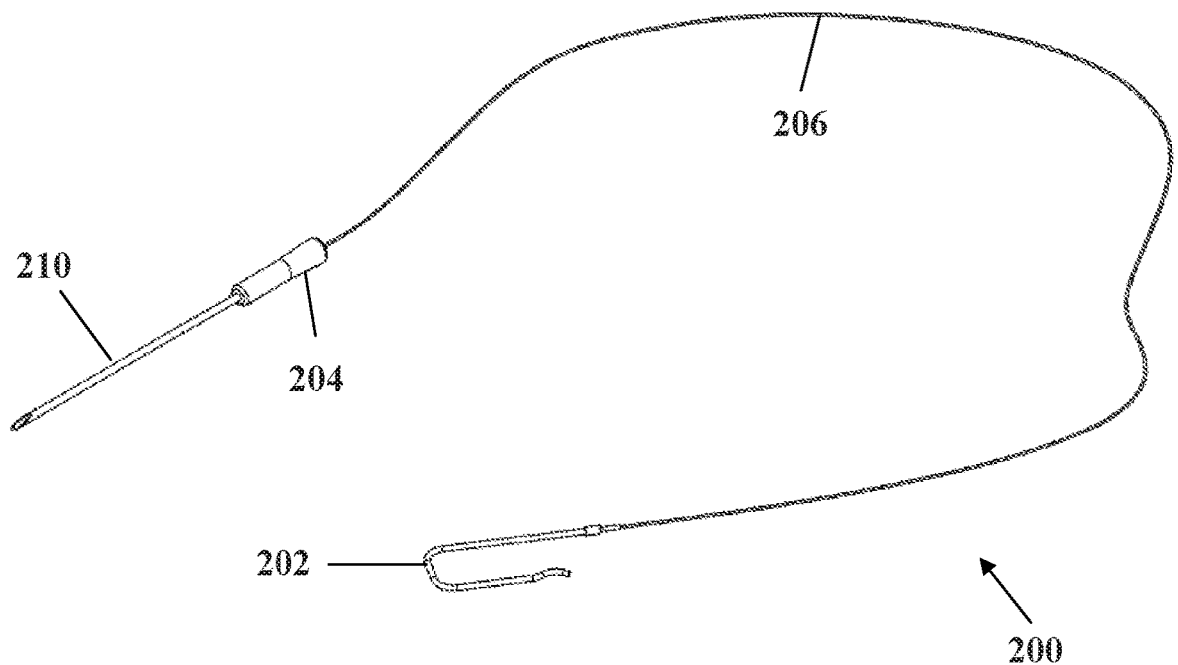
Figure 6:
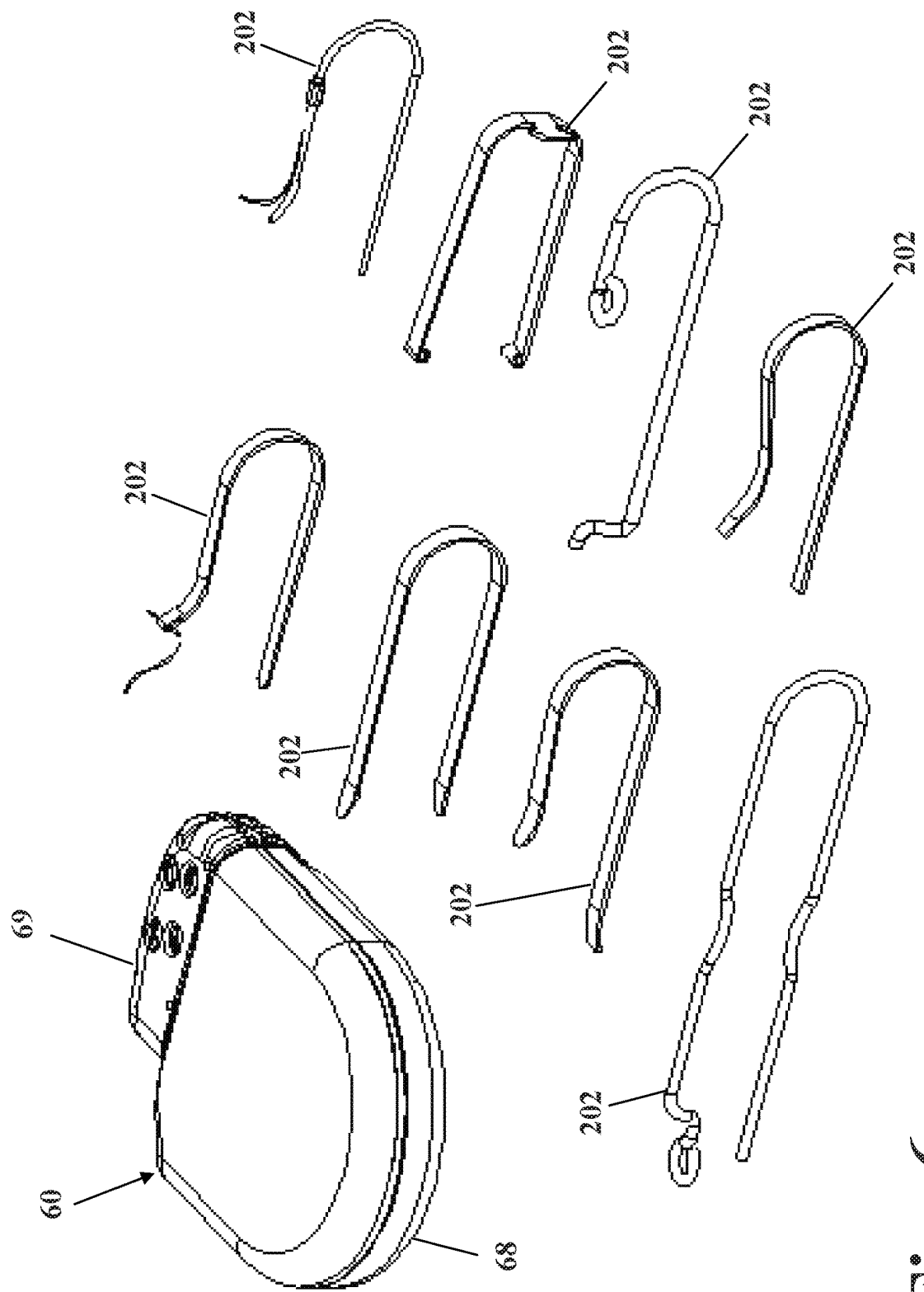
FIG. 6 is an isometric view of portions of various embodiments of implant adapters according to the present invention.

Referring now generally to FIGS. 5A-6, an implant adapter 200 is depicted for use during a mapping procedure to implant baroreflex therapy system 90. In one embodiment, implant adapter 200 generally includes a first end 202 configured to conductively couple with pulse generator housing 68, a second end 204 and a conductive means 206 configured to extend between first end 202 and second end 204.

First end 202 is constructed of suitable biocompatible electrically conductive materials, such as stainless steel, titanium or platinum. First end 202 is configured to releasably and conductively couple to pulse generator housing 68 to provide a temporary electrical connection for the mapping procedure. A variety of embodiments of first end 202 are depicted in FIGS. 5A-6, comprising various configurations of clips, clamps, and straps, although it will be appreciated by one of skill in the art that first end 202 may comprise a variety of shapes, sizes and configurations. First end 202 may be biased so as to provide a snug fit against housing 68. The various embodiments of first end 202 depicted should be considered merely exemplary, and not an exhaustive or limiting representation.

Referring now to specific embodiments of first end 202 of implant adapter 200, in FIG. 5A first end 202 comprises a strap configured to wrap around pulse generator housing 68 of control system 60. The strap may be constructed of conductive, or non-conductive material, but includes a button of conductive material in communication with the conductive means 206 and in contact with housing 68. In FIGS. 5B and 5C, first end 202 comprises a clip constructed from an electrically conductive material which is configured to slip onto housing 68, and may be biased to urge first end 202 into contact with housing 68. In FIG. 5D, first end 202 comprises a coiled spring constructed from an electrically conductive material which is configured to wrap around housing 68.

Referring to FIG. 5E, first end 202 comprises a strap or band constructed from an electrically conductive material configured to wrap around housing 68, and in communication with a conductive means 206 comprising a plate of electrically conductive material which is configured to directly couple with a temporary reference element 210. Temporary reference element 210 may alternately be referred to as a reference electrode. In one embodiment, element 210 comprises an anode and electrode 112 comprises a cathode. In another embodiment, element 210 comprises a cathode and electrode 112 comprises an anode. In FIG. 5F, first end 202 comprises a strap or band constructed from an electrically conductive material configured to wrap around housing 68, and in communication with a conductive means 206 comprising a plate of electrically conductive material which is configured to indirectly couple with temporary anode 210 by way of an alligator clip or similar means.

Referring to FIG. 5G, first end 202 comprises a clip constructed from an electrically conductive material which is configured to slip onto housing 68, and may be dimensioned and/or biased to urge first end 202 into contact with housing 68. As depicted in FIG. 6, various alternate configurations of first end 202 are within the spirit and scope of the present invention.

In one embodiment, second end 204 comprises a connection means configured to couple to a temporary anode 210, which is configured to replicate the anode of implantable baroreflex therapy system 90. In another embodiment, second end 204 itself is configured to comprise the temporary anode 210, as depicted in FIG. 5H.

In one embodiment, temporary anode 210 comprises a needle, metal catheter, or the like, having an outer diameter of between about 1.0 mm and about 4.0 mm, or between about 20 gauge to about 8 gauge. More particularly, temporary anode 210 may include an outer diameter between about 1.0 mm and about 2.0 mm, or between about 19 gauge to about 14 gauge. Even more particularly, temporary anode 210 may be about 18 gauge or 16 gauge. While other sized needles may be utilized, needles within the above diameter ranges have been found to typically be readily available, inexpensive and suitable for use according to various embodiments of the present invention. A temporary anode sized and configured as described herein will adequately replicate the electrical characteristics of pulse generator housing 68 for the purposes of conducting a mapping procedure.

In use, temporary anode 210 comprising for example a needle is inserted subcutaneously. The needle 210 may be inserted orthogonal to the surface of the patient's skin, or may be inserted generally parallel beneath the surface of the skin, or at other angles therebetween as desired. In one embodiment, needle 210 may be inserted within a range between generally parallel to the surface of the skin up to an angle of about 30 degrees from the surface of the skin. According to various embodiments, needle 210 may need to be inserted subcutaneously between about 5 mm to about 80 mm in order to provide sufficient impedance for the mapping procedure. More particularly, needle 210 may need to be inserted subcutaneously between about 10 mm to about 40 mm below the surface. In other embodiments, temporary anode 210 may comprise an electrode disk or conductive instrument, which is configured to be temporarily inserted below the skin of a patient through a small incision created during the mapping procedure. The use of temporary anodes in the form of cutaneous, or external, electrodes has not been found suitable due to the relatively high impedance of the skin of a patient.

In one embodiment, temporary anode 210 is inserted subcutaneously generally in the area where a pocket will later be created for implantation of the pulse generator housing 68. The pocket location is suitable for ease of access, relatively low risk of stimulating other tissues during the mapping procedure, and simplicity of working in the same area where the pulse generator will ultimately be implanted. Alternately, temporary anode 210 may be inserted in any other location deemed suitable.

Conductive means 206 may be constructed of suitable biocompatible electrically conductive materials, such as stainless steel, titanium or platinum, and is configured to be of a length sufficient to allow housing 68 to be placed in a desired location during the mapping procedure. In one embodiment, conductive means 206 may be of a length between about six to twelve inches, although other lengths may be selected as desired. In another embodiment depicted in FIGS. 5E-5F, conductive means 206 may comprise a plate configured to electrically communicate with a temporary anode 210.

Figure 7:
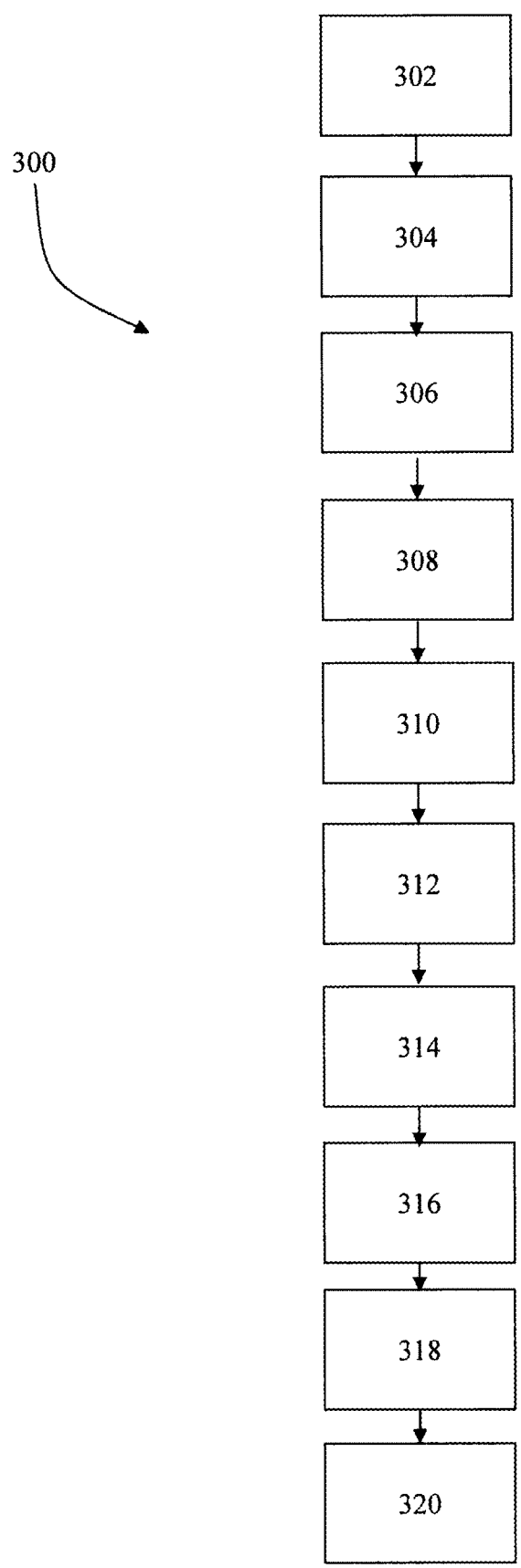
FIG. 7 is a flowchart depicting an embodiment of a method of the present invention.
Figure 8:
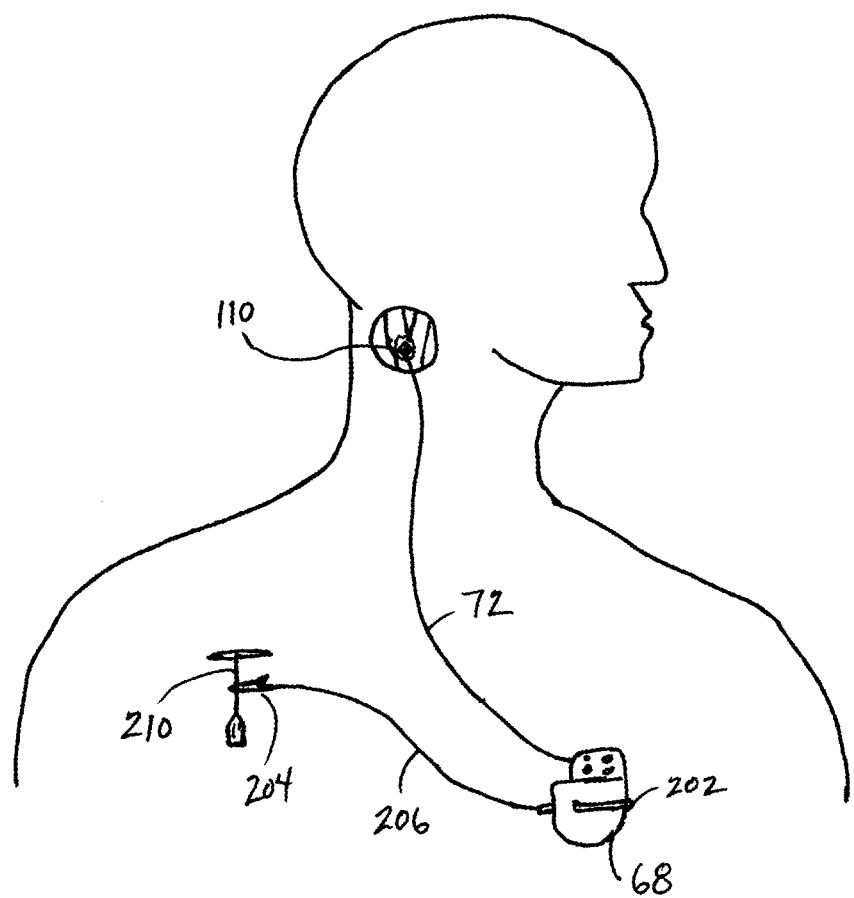
FIG. 8 is a schematic depiction of an implant adapter in use during a mapping procedure according to an embodiment of the present invention.

Referring now to FIGS. 7-8, a method 300 of implanting a baroreflex therapy system 90 according to embodiments of the present invention is depicted. In step 302, a surgeon first identifies and marks the desired implant location. Without limitation, one example of a suitable site for delivering baroreflex activation therapy is the carotid sinus. The general implant location may be obtained with the use of ultrasound, or other imaging techniques known to those skilled in the art. In step 304, a small incision is made on the patient in the identified region. In one embodiment, the length of the incision should be about four inches or less. In another embodiment, the length of the incision should be about two inches or less. The size of the incision needed will be determined by the location of the implant and the specific patient, however the configuration of electrode structure 110 of the baroreflex therapy system 90 described herein allows for a minimally invasive incision. The incision depicted in FIG. 8 is exaggerated for easier understanding and is not necessarily to scale.

Determining an optimal location to affix electrode structure 110 is critical for effective therapy, as differences in location of as little as 1 mm can make a medically relevant difference in the effectiveness of the baroreceptor activation. As described in U.S. Pat. No. 6,850,801 to Kieval et al., incorporated by reference above, the degree of baroreceptor activation at various positions around the circumference of the carotid sinus is non-homogenous and unpredictable. This suggests the distribution of baroceptors within the walls of blood vessels is variable, and therefore a mapping procedure is undertaken as part of the implant procedure. In preparation for the mapping procedure, in step 306 the electrode structure is releasably coupled to an implant tool, such as described in U.S. Pat. No. 8,437,867 to Murney et al., incorporated by reference above.

In step 308, temporary anode 210 is inserted subcutaneously, generally in the area where a pocket will later be created for pulse generator housing 68.

In step 310, the first end 202 of adapter 200 is releasably coupled to housing 68 of the pulse generator, which itself may be placed on the chest of the patient or otherwise suitably supported within the sterile field for the mapping procedure. The use of an insulating material may be used beneath the pulse generator to prevent conductance into the surface upon which the pulse generator is placed. If conductive means 206 is separate from second end 204, then step 310 also includes coupling second end 204 of adapter 200 to conductive means 206. With adapter 200 coupled to housing 68, temporary anode 210 acts as the reference electrode during the mapping procedure.

In step 312, the mapping procedure is conducted. The implant tool is used to introduce the electrode structure into the incision until the electrode structure is in contact with the target implant vessel, such as for example the carotid sinus. Generally, input device (programmer) 64 is utilized to cause the pulse generator to provide a stimulation signal to electrode structure 110, and one or more patient responses to the signal is then measured and/or logged. Using implant tool 154, electrode structure 110 is moved around the contours of the carotid sinus to different positions, with additional stimulation signals delivered and patient responses measured at each position. Patient physiological responses that may be measured during a mapping procedure include blood pressure, heart rate, cardiac output, stroke volume or other cardiac parameters, EEG, respiration parameters, pulse oximetry, intrinsic nerve activity, vessel wall acceleration or other vessel wall motion measurements, reflected arterial pressure waves, indices of vascular stiffness, direct measures of sympathetic and parasympathetic nervous system activity, plasma concentrations of neurohormones or other biomarkers, for example.

Once a suitable location for implantation has been located, in step 314 the implant tool is removed, and electrode structure 110 is fixed at the site. Numerous fixation means and techniques are provided for securing electrode structure 110 to the implant site, and may include passive or active fixation. Electrode structure 110 may be sutured directly to a blood vessel, for example. Preferably at least two sutures are utilized to insure electrode structure 110 is secure and in sufficient electrical contact with the blood vessel. Other fixation means may be used, such as described in U.S. Pat. No. 8,437,867 to Murney et al., incorporated by reference above.

In step 316, the lead 72 and pulse generator are disconnected, and the pulse generator is temporarily set aside but remains within the sterile field. A pocket is created in the chest of the patient for implanting the pulse generator. In step 318, a path may be tunneled for lead 72 from the electrode implant location to the pulse generator pocket location. If lead 72 includes a strain relief attachment tab 73, the tab is then sutured in place near electrode structure 110. Lead 72 may then be re-connected to the pulse generator.

Figure 9:
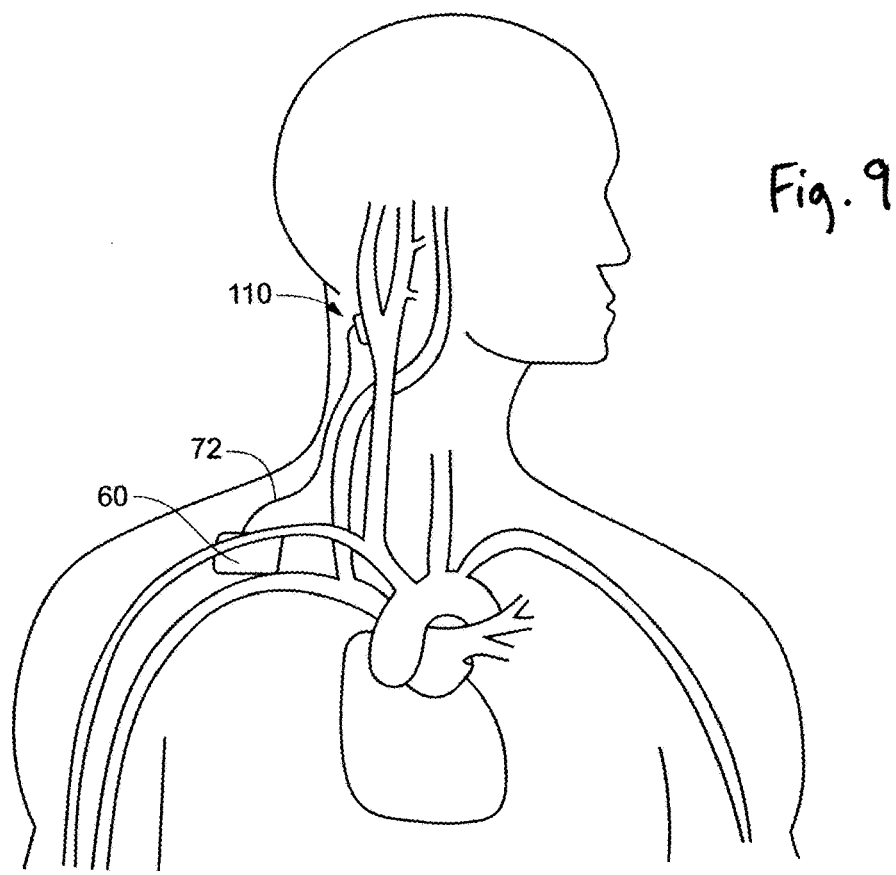
FIG. 9 is a schematic representation of a baroreflex activation system according to an embodiment of the present invention implanted on a carotid sinus within a patient.
Figure 10:
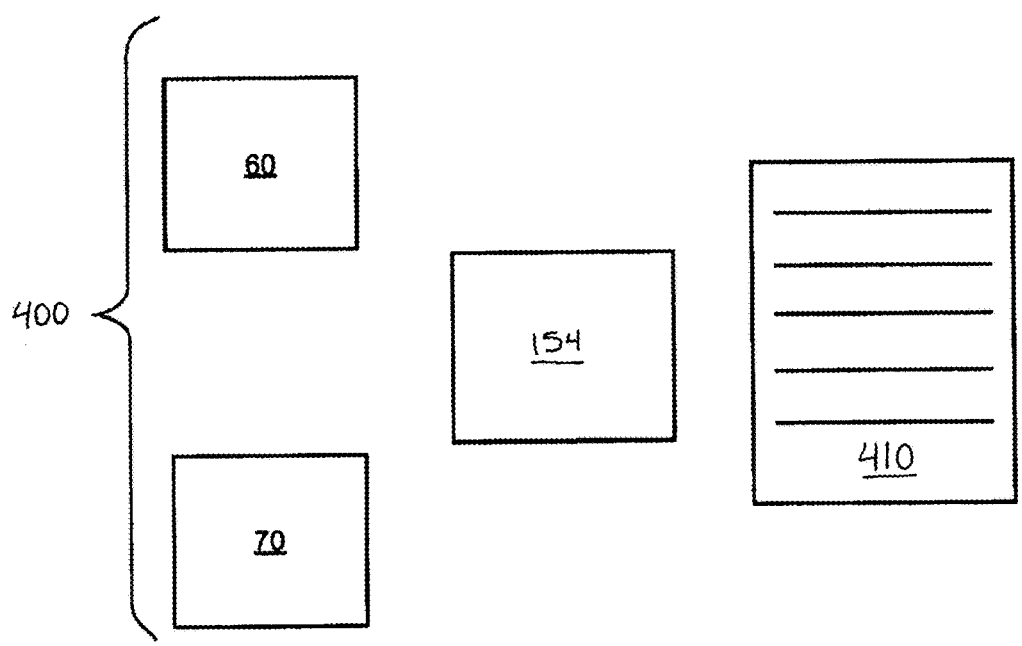
FIG. 10 is a schematic representation of a kit according to an embodiment of the present invention.

Finally, in step 320 the pulse generator is implanted within the pocket and the incisions are closed. FIG. 9 is a schematic illustration of the baroreflex activation system 90 fully implanted within the patient.

The order of the steps presented herein should not be considered limiting, as certain steps may be omitted, combined, or carried out in an order other than that presented here. In the event baroreflex therapy system 90 includes multiple baroreceptor activation devices, additional mapping procedures are conducted according to the procedures described herein.

In a further embodiment, the present invention comprises a kit 400 which includes an implantable pulse generator in the form of a control system 60 within a housing 68, a baroreflex activation device 70 having at least one electrode structure 110 and coupled to the control system, an optional implant tool 154, and a set of instructions 410. Instructions 410 may be for implanting, programming and/or operating the system and may be recorded on a tangible medium or may comprise indications linking a user to electronically accessible instructions 410. Instructions 410 may include instructions for implanting electrode structure 110 and the baroreflex activation therapy system 90 as described herein, including the use of an implant tool and/or a mapping procedure, and/or for programming, adjusting, modifying and/or operating control system 60. Instructions 410 may be provided to a user in compliance with government agency regulations or requirements for labeling of medical devices, for example the regulations described in Title 21 of the Code of Federal Regulations, Part 801. Kit 400 may be comprised of one or more hermetically sealed and sterilized packages.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions. Although described mainly in the context of electrical activation of baroreceptors for mapping and chronic therapy, alternate means of activation may also be utilized, such as localized pressure or suction, chemical activation, thermal activation, optical activation, mechanical activation, or other means of activation such as described in the patents and publications incorporated by reference herein.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. A system, comprising:
a control system contained within an implantable housing;
a header coupled with the implantable housing;
an electrical lead, coupleable to the control system via the header;
a monopolar electrode coupled to the electrical lead, the monopolar electrode being configured for implantation in contact with at least a portion of a blood vessel;
a reference electrode, configured to be temporarily inserted subcutaneously in a patient; and
an implant adapter, including a first end coupleable to an electrically conductive exterior surface of the implantable housing and a second end coupleable to the reference electrode, wherein the first end and the second end of the implant adapter are conductively coupled,
wherein the control system is configured to perform a mapping procedure in response to an instruction from an external programmer, the mapping procedure using the monopolar electrode as a cathode and the reference electrode as an anode.

2. The system of claim 1, wherein the control system is programmed to deliver a baroreflex therapy via the monopolar electrode to a baroreceptor within a wall of the blood vessel.

3. The system of claim 1, wherein the reference electrode comprises a needle.

4. The system of claim 1, wherein the control system is configured to deliver a baroreflex therapy having a voltage between 1 and 100 volts.

5. The system of claim 1, wherein the second end of the implant adapter comprises the reference electrode.

6. The system of claim 1, wherein the first end of the implant adapter includes a strap that wraps around the implantable housing, the strap including a button of conductive material that contacts the implantable housing.

7. The system of claim 1, wherein the first end of the implant adapter includes a conductive strap configured to wrap around the implantable housing.

8. The system of claim 1, wherein the first end of the implant adapter includes a conductive clip configured to wrap at least partially around the implantable housing to provide an electrical connection between at least one surface of the conductive clip and the electrically conductive exterior surface of the implantable housing.

9. The system of claim 8, wherein the clip is configured to contact at least two sides of the electrically conductive exterior surface of the implantable housing.

10. The system of claim 8, wherein the second end of the implant adapter comprises the reference electrode.

11. The system of claim 1, wherein the first end of the implant adapter includes a conductive coiled spring configured to wrap at least partially around the implantable housing.

12. The system of claim 1, wherein the second end of the implant adapter includes an alligator clip configured to couple with the reference electrode.

\* \* \* \* \*